(12) United States Patent
Sonnleitner

(10) Patent No.: US 8,569,716 B2
(45) Date of Patent: Oct. 29, 2013

(54) OPTOELECTRONIC SENSOR SYSTEM

(75) Inventor: Max Sonnleitner, Linz (AT)

(73) Assignee: ASMAG-Holding GmbH (AT)

( * ) Notice: Subject to any disclaimer, the term of this patent is extended or adjusted under 35 U.S.C. 154(b) by 441 days.

(21) Appl. No.: 12/668,734

(22) PCT Filed: Jul. 12, 2007

(86) PCT No.: PCT/EP2007/006354
§ 371 (c)(1),
(2), (4) Date: Jul. 2, 2010

(87) PCT Pub. No.: WO2009/006928
PCT Pub. Date: Jan. 15, 2009

(65) Prior Publication Data
US 2010/0308233 A1    Dec. 9, 2010

(51) Int. Cl.
*G01J 1/58* (2006.01)
(52) U.S. Cl.
USPC ..................................................... 250/458.1
(58) Field of Classification Search
USPC ............... 250/208.1, 458.1, 459.1; 422/82.11
See application file for complete search history.

(56) References Cited

U.S. PATENT DOCUMENTS

| 7,058,244 B2 | 6/2006 | Iida et al. |
| 2003/0025084 A1* | 2/2003 | Honda et al. ............. 250/370.11 |
| 2006/0051244 A1 | 3/2006 | Lehmann et al. |

FOREIGN PATENT DOCUMENTS

| JP | 2004279078 A | 10/2004 |
| JP | 2005189237 A | 7/2005 |
| WO | 00/63677 A1 | 10/2000 |
| WO | 03102554 A1 | 12/2003 |
| WO | 2004013616 A1 | 2/2004 |
| WO | 2006/026796 A1 | 3/2006 |
| WO | 2006/131225 A1 | 12/2006 |
| WO | 2007054710 A2 | 5/2007 |

OTHER PUBLICATIONS

International Search Report, PCT/EP2007/006354, dated Jul. 3, 2008.
Wei et al., Biophotonics, The Second Asian and Pacific Rim Sympos lum on Taipei, Taiwan Dec. 14-17, 2004; pp. 236-237.

* cited by examiner

*Primary Examiner* — Mark R Gaworecki
(74) *Attorney, Agent, or Firm* — Lerner, David, Littenberg, Krumholz & Mentlik, LLP

(57) ABSTRACT

The underlying objective is to create an optoelectronic sensor system which illuminates the specimen homogenously and only allows produced fluorescent light to reach the photoactive layer. The objective is achieved substantially by creating a total reflection layer for the introduced light before or above the optoelectronic sensor layer. This can be applied in all fields in which microarray biochips are used.

15 Claims, 1 Drawing Sheet

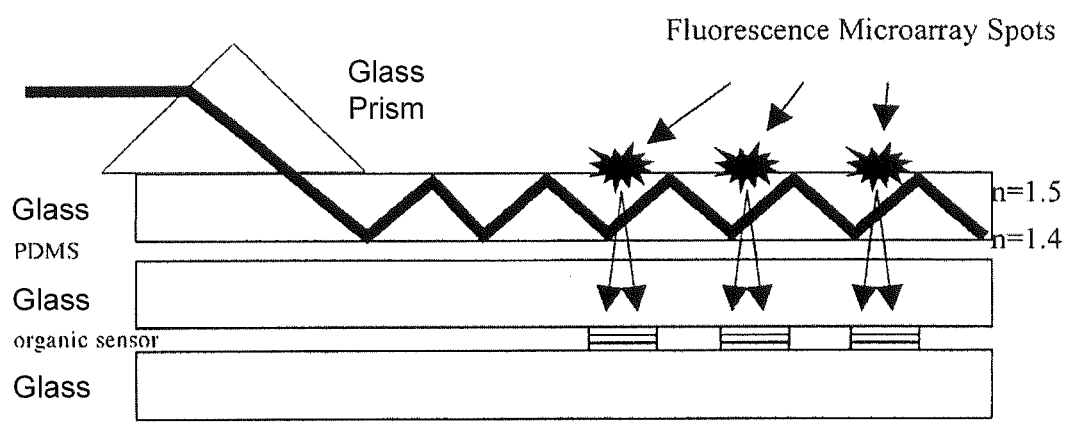

OPTOELECTRONIC SENSOR SYSTEM

CROSS REFERENCE TO RELATED APPLICATIONS

The present application is a national phase entry under 35U.S.C. §371 of International Application No. PCT/EP2007/006354, filed Jul. 12, 2007, published in German. The disclosure of said application is incorporated by reference herein.

The invention relates to an optoelectronic sensor system for stimulating and detecting specimens.

In the fields of medicine, pharmaceutics, biochemistry, genetics or microbiology the use of microarray biochips is increasing in significance. In the briefest time such a chip supplies the results of several ten hundred thousand reactions. Microarray biochips consist of a substrate material on which biological specimen molecules are fixed in a defined manner in a high number and density in so-called microarrays. Each of these points or spots replaces a reaction vessel.

For the actual investigation fluorescent-based methods are used for example, in which the specimens are marked, so that—after stimulation by a light source, for example a laser—fluorescent signals are formed which can be detected. Conventional microarray selection systems use lasers for stimulating the fluorescence point by point or gas discharging lamps (mercury, xenon, metal halogenide) for stimulating the fluorescence over a large surface. All systems during the selection process have to scan the specimen or the light source and thus require precise traversing mechanics. In addition, such systems require complex optical systems for displaying the fluorescence signals on the detector. These factors prevent the required miniaturising and also the inexpensive manufacture of the selection systems.

From WO 2006/026796 a device is known by means of which biochemical specimens such as microarrays can be evaluated.

The latter consists of a specimen substrate as well as an image-detecting device. Said image-detecting device comprises a photoactive layer on the basis of organic semiconductors between two electrode layers, of which the electrode layer between the photoactive layer and the specimen is designed to be light-permeable at least in some areas. Said image-detecting device can be attached directly onto the surface of the biochip opposite the microarray and thus makes precise traversing mechanics and expensive imaging optical systems found in conventional selection systems unnecessary.

To use this image-detection system for the fluorescence-based selection of biochemical specimens without traversing mechanisms and imaging optics the following requirements have to be met:
- the specimen has to be illuminated homogenously with stimulating light,
- only the produced fluorescent light is allowed to reach the photoactive layer,
- the distance between the fluorescing specimen (in the microarray spots) and sensor has to be the same as the centre-to-centre spacing of the microarray spots to avoid crosstalking problems between the pixels.

The objective of the invention is therefore to create an optoelectronic sensor system, which satisfies these conditions.

Re homogenous illumination:

If the image detecting system is arranged directly opposite the specimen on the biochip the specimen no longer has to be scanned over. However, such a structure requires the specimen to be illuminated homogenously with sufficiently high stimulation intensity.

Re blocking the direct or scattered stimulating light:

Each fluorescence-based measuring system requires a light source for stimulating the fluorescence. The intensity of this stimulating light is thus many times greater than that of the resulting fluorescent light. For reliable measurement results only the fluorescent light can reach the photoactive layer, but no direct or scattered stimulating light, as this would result in measurement errors.

Re spacing between the specimen and sensor:

Clear allocation of the signal detected in the image-detecting device to the fluorescence of a microarray spot is a requirement for correct measurement results. Typically the microarray spot diameters are 100-200 µm with a centre-to-centre spacing of about 300 µm. Therefore, in order to avoid so-called signal crosstalking directly on the biochip with an image-detecting device arranged opposite the microarray, the distance between the specimen and image-detecting device has to be the same as the spot distance.

These objectives are achieved according to the invention by an optoelectronic sensor system, with a surface for applying the specimens and an underlying layer system with a transparent first layer with a first refractive index, into which light can be introduced for stimulating the specimen, and an adjoining second layer with a second, smaller refractive index for generating total reflection of the introduced light and a resulting spreading planar light wave in the first layer and an optoelectronic sensor layer lying underneath the second layer, said sensor layer consisting of one or more semiconductor layers between two electrode layers, of which the electrode layer facing the specimen is designed to be light-permeable at least in sections.

The total reflection on the layer with a smaller refractive index means that the stimulating light only spreads in the first layer with the slightly greater refractive index.

The biological specimens are located on the upper side of said layer. Total reflection occurs there and a so-called evanescent field is formed with a penetration depth of 100 to 500 nm, which only stimulates the molecules close to the surface selectively. The fluorescent signals or even luminescent signals then emitted by the specimens can be received unhindered by the optoelectronic sensor layer without measurement errors being caused by scattered light.

Preferably, the stimulating light beam is introduced in that on the first layer a prism or grid is arranged for introducing the light.

According to an advantageous embodiment, the layer is made from polydimethylsiloxane (PDMS) with a smaller refractive index.

An absorbing pigment/colorant can be added to the latter as an optical filter.

Preferably, between the second layer and optoelectronic sensor system there can be an additional layer with optical filter properties or only partial light permeability.

The photosensitive optoelectronic layer can be designed on the basis of an organic semiconductor.

An optoelectronic sensor system according to the invention can be characterised by the following structure:
- a first glass substrate for applying microarray spots on its surface
- a second glass substrate as a substrate for the sensor
- a third glass substrate as an encapsulation for the sensor
- a photosensitive optoelectronic layer between the second and the third glass substrate consisting of one or more semiconductor layers between two electrode layers, of which the electrode layer facing the specimen is designed to be at least partly light-permeable, a PDMS intermediate layer between the first and the third glass substrate and a prism arranged on the surface of the first glass substrate which prism introduces the light beam emitted by a light source at a specified angle into the first glass substrate, where it is guided under total reflection to the PDMS intermediate layer in the first glass substrate as a planar lightwave.

This structure is also represented schematically in the drawing.

The angle of entry of the light beam into the first glass substrate is preferably above the threshold angle for total reflection between glass and PDMS, i.e. above 69°. (Refractive index: glass n1=1.52, PDMS: n2=1.42→angle for total reflection: α=arc sin(n2/n1)=69.1)°.

An optoelectronic sensor system with this structure is characterised by its small dimensions, i.e. the thickness of the first glass substrate can for example be 50-200 µm, of the first glass substrate together with the third glass substrate and the PDMS intermediate layer about 300 µm and the total thickness of the sensor can be about 1 mm.

A laser, LED or OLED can be used as the stimulating light source with a wavelength of 300-650 nm.

The invention claimed is:

1. An optoelectronic sensor system for stimulating and detecting specimens, with a surface for the application of the specimens and an underlying layer system with a transparent first layer with a first refractive index, into which light can be introduced for stimulating the specimen, and an adjoining second layer with a second smaller refractive index for generating a total reflection of the introduced light and a resulting spreading planar lightwave in the first layer and an optoelectronic sensor layer lying under the second layer comprising one or more semiconductor layers between two electrode layers, of which the electrode layer facing the specimen is designed to be at least partly light permeable, further comprising two glass layers wherein the optoelectronic sensor layer is located between two glass layers.

2. The optoelectronic sensor system according to claim 1, wherein on the first layer a prism or grid is arranged for introducing the light.

3. The optoelectronic sensor system according to claim 1, wherein the first layer is made of glass.

4. The optoelectronic sensor system according to claim 1, wherein the first layer has a thickness of 50-300 µm.

5. The optoelectronic sensor system according to claim 1, wherein the second layer is made of polydimethylsiloxane (PDMS).

6. The Optoelectronic sensor system according to claim 5, wherein a substance is added to the second layer which substance changes the optical transmission behaviour of said layer.

7. The optoelectronic sensor system according to claim 6, wherein
the added substance is an absorbing pigment or a colorant.

8. The optoelectronic sensor system according to claim 1, wherein additional optical filter layers are located between the second layer and the optoelectronic sensor layer.

9. An optoelectronic sensor system, comprising:
a first glass substrate for applying microarray spots on its surface,
a second glass substrate as a substrate for the sensor,
a third glass substrate as encapsulation for the sensor,
a photosensitive optoelectronic layer lying between the second and the third glass substrates including one or more semiconductor layers between two electrode layers, of which the electrode layer facing the specimen is designed to be at least partly light-permeable,
a PDMS intermediate layer between the first and the third glass substrate, and
a prism arranged on the surface of the first glass substrate, which introduces the lightbeam emitted from a light source at a specified angle into the first glass substrate, where it is guided under total reflection to the PDMS intermediate layer.

10. The optoelectronic sensor system according to claim 9, wherein the entry angle of the light beam into the first glass substrate is greater than the critical angle for total reflection between glass and PDMS.

11. The optoelectronic sensor system according to claim 9, wherein the thickness of the first glass substrate is 50-200 µm, and of the first glass substrate together with the third glass substrate and the PDMS intermediate layer about 300 µm and the total thickness of the sensor is about 1 mm.

12. The optoelectronic sensor system according to claim 9, wherein the photosensitive layer is applied onto the second glass substrate.

13. The optoelectronic sensor system according to claim 9, wherein the stimulating light source comprises a laser, LED or OLED for producing light having a wavelength of 300-650 nm.

14. The optoelectronic sensor system according to claim 9, wherein the photosensitive layer is formed on the basis of an organic semiconductor.

15. An optoelectronic sensor system comprising a light source for stimulating specimens, with a surface for the application of the specimens and an underlying layer system with a transparent first layer with a first refractive index, into which light can be introduced for stimulating the specimen, and an adjoining second layer with a second smaller refractive index for generating a total reflection of the introduced light and a resulting spreading planar lightwave in the first layer and an optoelectronic sensor layer lying under the second layer comprising one or more semiconductor layers between two electrode layers, of which the electrode layer facing the specimen is designed to be at least partly light permeable,
wherein the stimulating light source comprises a laser, LED or OLED for producing light having a wavelength of 300-650 nm, and
wherein the photosensitive layer is formed from an organic semiconductor.

* * * * *